United States Patent [19]

Kimura et al.

[11] Patent Number: 4,595,479

[45] Date of Patent: Jun. 17, 1986

[54] MODIFIED ELECTRODE

[75] Inventors: Yasuhiro Kimura, Kawasaki; Katsumi Niki, Yokohama, both of Japan

[73] Assignee: Ajinomoto Co., Inc., Yokohama, Japan

[21] Appl. No.: 543,295

[22] Filed: Oct. 19, 1983

[30] Foreign Application Priority Data

Nov. 9, 1982 [JP] Japan .................................. 57-196608
Jul. 21, 1983 [JP] Japan .................................. 58-133103

[51] Int. Cl.$^4$ ............................................. C25B 11/12
[52] U.S. Cl. ................................. 204/294; 204/290 R
[58] Field of Search ..................... 204/290 R, 294, 400

[56] References Cited

U.S. PATENT DOCUMENTS 4,414,080  11/1983  Williams et al. ................ 204/290 R

OTHER PUBLICATIONS

Berezin et al., Chem. Abstracts, vol. 85, No. 22, Nov. 29, 1976, p. 196, col. 2, Abstract No. 163224v.

*Primary Examiner*—John F. Niebling
*Assistant Examiner*—Terryence Chapman
*Attorney, Agent, or Firm*—Oblon, Fisher, Spivak, McClelland & Maier

[57] ABSTRACT

A chemically modified electrode comprising a pyrolytic graphite surface, wherein the basal plane of graphite is exposed on said surface and a redox/adsorption electron mediator is irreversibly absorped directly onto the basal plane of graphite on said surface, is disclosed along with methods of using this electrode.

5 Claims, No Drawings

MODIFIED ELECTRODE

DETAILED DESCRIPTION OF THE INVENTION

This invention relates to a novel electrode derived from an electrically conducting solid electrode by modification of the surface thereof and to applications of the novel electrode.

It has been well known that electrically conducting solid electrode surfaces can be modified by redox polymers. However, the activity of this modified electrode varies with the degree of polymerization of the redox polymers, and the electrode is active only in strongly acidic solutions because electron mediators can be coupled with polymers only in a strongly acidic solution.

The electrode which has polyvinyl pyridine, for example, immobilized on pyrolytic graphite has been proposed to the art (as reported in N. Oyama et al., J. Electrochem. Soc., 127, 640 (1980), for example). It has a disadvantage that its effective use is obtained only under a strongly acidic condition and the substance to be immobilized is limited to that of a cationic type.

It has been also well known that an electron mediator such as methyl viologen is used in the form of a solution or a suspension with an unmodified electrode or with a chemically modified electrode. In this case, a large amount of an electron mediator has to be used and, in some cases, an electrochemically inactive material, which may decrease the current efficiency, has to be added to the solution.

An object of this invention is to provide a novel modified electrode which overcomes the various disadvantages suffered by the conventional art, warrants ease of manufacture and handling, and finds extensive utility in a rich variety of applications.

The inventors of the present invention have already made separate inventions, including ones which relate to an electrode characterized by having an aromatic-group-containing, strongly acidic, cation-exchange resin and a nitrogen-containing electron mediator immobilized on the surface of a solid conductive electrode and to an electrochemical bio-sensor using the electrode. The particular inventions have issued from the discovery that a modified electrode having a nitrogen-containing electron mediator stably immobilized therein can be obtained through the medium of the aromatic-group-containing, strongly acidic, cation-exchange resin. Japanese Pat. Appln. No. 36,870/1982, and the corresponding U.S. pat. appln. Ser. No. 473,207 and European Pat. Appln. No. 83301134.9.

The inventors, after a further study, have found that a stable chemically modified electrode is easily obtained by selecting, as an electron mediator capable of responding to a biological substance without intervention of any such aromatic group-containing strongly acidic, cation-exchange resin, a compound having some particular chemical structure such as viologen dye, bipyridine, phenanthroline, 1-methoxy-5-methylphenazenium methyl sulfate or N-methylphenazenium methyl sulfate and combining this mediator compound with a pyrolytic graphite in which the basal plane of graphite is exposed and that this modified electrode exhibits an excellent electrochemical response to biological substances such as hemoproteins, NADH, NADPH and the like. The present invention has been perfected on the basis of these findings. To be specific, this invention relates to a chemically modified electrode comprising an electrically conducting solid electrode which is pyrolytic graphite with an exposed basal plane of graphite and an electron mediator compound immobilized on the surface of said electrical conducting solid electrode.

Heretofore, quinones have often been used as an electron mediator for NADH and the like. But, prior-art compounds such as those shown in FIG. 1 in which the redox site (A) and the adsorption site (B) are apart from one another in the molecule will not clearly oxidize NADH because of their high overvoltage (T. Kuwana et al., J.A.C.S., 105, 1805 (1983)). The expression "the adsorption site" is herein used to mean the adsorption site at which the molecule is adsorbed, i.e., is immobilized by adsorption, on the surface of an electrical conducting solid electrode. The expression "the redox site" is self-explanatory.

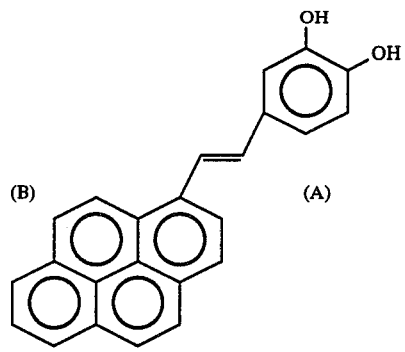

FIG. 1

On the contrary, electron mediator compounds of this invention, which are immobilized on the surface of an electrical conducting solid electrode which is pyrolytic graphite exposing the basal plane of graphite, have a particular chemical structure in which the redox site and the adsorption site are not apart from one another, i.e., both sites are fused, in the molecule. Thus, the molecules are not only irreversibly adsorbed onto the basal plane of graphite but also are markedly stabilized.

For example, N-methyl-phenazenium methyl sulfate, an example of the mediator compounds of this invention, shows both the redox function and adsorption function, but both functions are not attributable to definitely different sites in the molecule. It has a particular chemical structure, as shown in FIG. 2, in which the redox site and the adsorption sites are not differentiated.

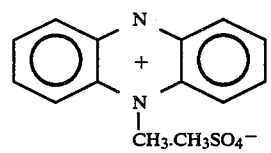

FIG. 2

An electron mediator of this invention with such particular chemical structure has an advantage that overvoltage for NADH and the like is very low.

An (electron) mediator (compound) of this invention having the above-explained particular chemical structure may hereinafter be referred to simply as "a redox-/adsorption (electron) mediator (compound)" in this specification and the claim(s).

Examples of redox/absorption mediators include additionally viologen dye, bipyridine, phenanthroline, and 1-methoxy-5-methylphenazenium methyl sulfate.

For use in the present invention, any of the electrically conducting solid electrodes known to the art may be adopted. The carbon electrode of pyrolytic graphite abundantly exposing the basal plane of graphite such as, for example, the stress-annealed pyrolytic graphite made by U.C.C. (hereinafter referred to as "SAPG") may be cited as a desirable representative.

The electron mediator is to be selected from among redox/adsorption mediator compounds such as viologen dye, bipyridine, phenanthroline, 1-methoxy-5-methylphenazenium methyl sulfate and N-methylphenazenium methyl sulfate.

For example, the followings are to be added in connection with N-methylphenazenium methyl sulfate;

N-methylphenazenium methyl sulfate has heretofore been used in the form of aqueous solution and that in a dark place, but it is inconvenient to use it in a dark place. Further, it has been thought to be undesirable to use N-methylphenazenium methyl sulfate in aqueous solution under scattering light, because the compound is unstable and easily undergoes photochemical oxidation under light in a light place.

Therefore, although attempts have been made to change the compound to more stable derivatives, any methods of using it as such in a stable manner has not been found as yet.

According to the present inventor's findings, however, N-methylphenazenium methyl sulfate is satisfactorily adsorbed only onto the basal plane of graphite as a solid electrode and is remarkably stabilized, and exhibits an excellent electrochemical response to NADH-, NADPH and the like. Thus, it has become possible to provide a modified electrode which is stable and exhibits an excellent electrochemical response to biological substances.

The modified electrode of this invention can be easily produced by immersing a pyrolytic graphite carbon electrode exposing the basal plane of graphite as described above in an aqueous solution of a redox/adsorption electron mediator and, when necessary, subsequently washing and drying the impregnated carbon electrode. The amount of the redox/adsorption electron mediator to be immobilized on the surface of the carbon electrode is desired to be enough to form a monomolecular layer (amount of saturated adsorption), although, even when this amount is lower than the level of saturated adsorption, the modified electrode can be effectively used.

The electrode of this invention excels the conventional countertypes in the following points:

(1) The fabrication of the electrode is extremely simple because it only requires immersion of the carbon electrode in an aqueous solution of a redox/adsorption electron mediator. In addition, the consumption of the electron mediator during this immersion is notably small.

(2) The solution to be used for the electrode reaction is only required to possess a hydrogen-ion concentration in the neighborhood of neutrality, specifically in the range of pH 4 to 10. In other words, according to the present invention, any strongly acidic solution used inevitably with a conventional electrode, which has posed problems, is not required any longer. Thus, the modified electrode of the present invention is advantageously used as an electrode capable of responding to biological substances.

(3) The redox/adsorption electron mediator may be effectively used in the form of a monomer and can be quantitatively immobilized. Thus, there is no need for the preparation of a polymer or for uniformly controlling the degree of polymerization.

(4) Since the redox/adsorption electron mediator is immobilized in a monomolecular layer and retained stably in that state, this substance is consumed in a smaller amount with greater efficiency than when it is used in the form of a solution or suspension.

(5) The modified electrode warrants practical convenience in actual use because it is moderately hydrophilic and insusceptible of dissolution. N-methylphenazenium methyl sulfate is lacking in this general advantageous point, but, it has an advantage that it may be used more stably according to this invention than when it is used in the form of a solution.

As an electrode for fulfilling its function by responding to a biological substance, therefore, the modified electrode of the present invention proves to be an outstanding choice.

Since the electrode of the present invention is capable of generating an electric current in the presence of a biological substance liable to conjugation with the aforementioned redox/absorption electron mediator, it can be advantageously utilized as an electrode in a bioreactor. In this case, since the concentration of a biological substance and the magnitude of the electric current generated are in a linear relation, the modified electrode of the present invention can be utilized as a bio-sensor capable of quantitative analysis of a biological substance.

To be specific, the concentration of a specific biological substance in a given sample can be determined by fractionally separating the biological substance from the sample as by chromatography, then adding the isolated biological substance to a buffer solution of pH 4 to 10, placing the modified electrode of this invention in the resultant solution and placing an appropriate electrode as a counter electrode, applying an electric potential to the opposed electrodes, and measuring the magnitude of electric current consequently generated therein.

Examples of biological substance which respond to the redox/adsorption electron mediator include NADH, NADPH, cytochrome $C_3$, cytochrome C, hemoglobin, chlorophyl, and electron-transfer systems containing these substances.

Now, the present invention will be described more specifically below with reference to working examples. This invention is not limited to these working examples in any respect.

EXAMPLE 1

An SAPG electrode 5 mm in diameter was immersed for about 10 seconds in a 1-mM aqueous solution of 1-methoxy-5-methylphenazenium methyl sulfate and then washed and dried to produce a modified electrode.

With the use of this electrode, NADH was electrochemically oxidized. During the oxidation, the concentration of NADH and the magnitude of the electric current generated were measured. The results showed a linear relation between the two quantities as indicated in Table 1.

TABLE 1

| Concentration of NADH (g/liter) | Peak current ($\mu$A) |
|---|---|
| 0.68 | 12.6 |
| 0.50 | 9.1 |
| 0.35 | 6.3 |

TABLE 1-continued

| Concentration of NADH (g/liter) | Peak current (μA) |
| --- | --- |
| 0.17 | 3.3 |
| 0.0 | 0.0 |

EXAMPLE 2

An SAPG electrode 5 mm in diameter was immersed for about 10 seconds in a 1-mM aqueous solution of viologen dye and subsequently washed and dried to produce a modified electrode.

With the use of this electrode, reduced hemoglobin was electrochemically oxidized. During the oxidation, the concentration of hemoglobin and the magnitude of the electric current generated were measured. The results showed a linear relation between the two quantities as indicated in Table 2.

TABLE 2

| Hemoglobin (g/liter) | Peak current (μA) |
| --- | --- |
| 12.9 | 3.0 |
| 8.5 | 2.0 |
| 6.5 | 1.5 |
| 3.3 | 0.8 |
| 0.0 | 0.0 |

EXAMPLE 3

An SAPG electron 5 mm in diameter was immersed for about 10 seconds in a 1-mM aqueous solution of bipyridine and washed and dried to produce a modified electrode.

With the use of this electrode, ferrous cytochrome C was electrochemically oxidized. During this oxidation, the concentration of cytochrome C and the magnitude of the electric current generated were measured. The results showed a linear relation between the two quantities as indicated in Table 3.

TABLE 3

| Cytochrome C (g/liter) | Peak current (μA) |
| --- | --- |
| 8.0 | 9.1 |
| 6.0 | 6.9 |
| 4.0 | 4.6 |
| 2.0 | 2.3 |
| 0.0 | 0.0 |

EXAMPLE 4

When a modified electrode produced by following the procedure of EXAMPLE 1 was immersed in an aqueous solution containing NADH in a concentration of 50 g/liter and an electric potential was applied at a current density of about 10 $\mu A/cm^2$, NAD was substantially quantitatively obtained (about 90% of yield).

EXAMPLE 5

An SAPG electrode 5 mm in diameter was immersed for about 10 seconds in a 1-mM aqueous solution of methylviologen and washed and dried to produce a modified electrode.

In 20 ml of distilled water, 3 g of polyvinyl alcohol was amply dispersed at room temperature. The resultant mixture was gradually heated under conditions enabling thorough dissolution of the solute without boiling the mixture. The solution was then gradually cooled down to normal room temperature. Thereafter, bovine serum albumin was added, when necessary, to the solution at a ratio of 1% based on the weight of polyvinyl alcohol and dissolved therein. With this solution was mixed 0.28 g of *Anabaena cylindrica* suspension (having a chlorophyl content of about 3% by weight). The resultant mixed solution was uniformly spread in a thin layer on the aforementioned modified electrode and immediately dried in a desiccator kept in a dark room at 0° to 5° C. The dry weight was 2 mg.

In an aqueous phosphate buffer solution (pH 7), the electrode prepared as described above and a platinum electrode were set up. The magnitude of electric current generated between the electrodes was measured in the presence and absence of light (from a xenon lamp). Thus, the electric current was found to be 3 $\mu A/cm^2$ in the presence of light and zero in the absence of light. This fact implies the feasibility of photoelectric conversion.

EXAMPLE 6

An SAPG electrode 5 mm in diameter was soaked for about 10 seconds in an aqueous 1-mM solution of N-methylphenazenium methyl sulfate and then washed and dried to produce a modified electrode.

With the use of this electrode, NADH was electrochemically oxidized.

During the oxidation, the concentration of the NADH and the magnitude of the electric current generated were measured.

The result showed a linear relation between the two quantities as indicated in Table 4.

TABLE 4

| NADH concentration (g/liter) | Peak current (μA) |
| --- | --- |
| 0.68 | 12.0 |
| 0.50 | 8.5 |
| 0.35 | 5.6 |
| 0.17 | 3.3 |
| 0 | 0 |

EXAMPLE 7

An SAPG electrode 5 mm in diameter was soaked for about 10 seconds in an aqueous 1-mM solution of N-methylphenazenium methyl sulfate and then washed and dried to produce a modified electrode.

With the use of this electrode, NADPH was electrochemically oxidized.

During the oxidation, the concentration of the NADPH and the magnitude of the electric current generated were measured.

The result showed a linear reaction between the two quantities as indicated in Table 5.

TABLE 5

| NADPH concentration (g/liter) | Peak current (μA) |
| --- | --- |
| 2.0 | 19.7 |
| 1.1 | 10.2 |
| 0.5 | 4.8 |
| 0.2 | 2.1 |
| 0 | 0 |

EXAMPLE 8

When a modified electrode produced by following the procedure of EXAMPLE 6 was soaked in an aqueous solution containing NADH in a concentration of 50 g/liter and an electric potential was applied at a current density of about 10 $\mu$A/cm$^2$, NAD$^+$ was obtained in a high yield, i.e., about 85% yield.

What is claimed is:

1. A chemically modified electrode, comprising a pyrolytic graphite surface having a basal plane of graphite which is exposed on the said surface and a non-polymeric redox/adsorption electron mediator irreversibly adsorbed directly onto the said basal plane of graphite on the said surface.

2. The electrode of claim 1, wherein said pyrolytic graphite is stress-annealed pyrolytic graphite.

3. The electrode of claim 1, wherein the said redox-/adsorption mediator is at least one member selected from the group consisting of viologen dye, bipyridine, phenanthroline, 1-methoxy-5-methylphenazenium methyl and sulfate N-methylphenazenium methyl sulfate.

4. The electrode of claim 1, wherein said electrode further comprises at least one member selected from the group consisting of NADH, NADPH, cytochrome C$_3$, cytochrome C, hemoglobin and chlorophyl, conjugated with said redox/adsorption electron mediator.

5. The electrode of claim 1, wherein said electrode further comprises a layer of *Anabaena cylindrica* on said surface.

* * * * *

UNITED STATES PATENT AND TRADEMARK OFFICE
CERTIFICATE OF CORRECTION

PATENT NO. : 4,595,479

DATED : June 17, 1986

INVENTOR(S) : Kimura, Yasuhiro et al

It is certified that error appears in the above-identified patent and that said Letters Patent is hereby corrected as shown below:

On the title page assignee should read

-- (73) Assignee: Ajinomoto Co., Inc.,
    Tokyo, Japan --.

Signed and Sealed this

Fourteenth Day of October, 1986

[SEAL]

Attest:

DONALD J. QUIGG

*Attesting Officer*  *Commissioner of Patents and Trademarks*